US00PP37751P3

(12) United States Plant Patent
Olesen

(10) Patent No.: US PP37,751 P3
(45) Date of Patent: Oct. 13, 2026

(54) MINIATURE ROSE PLANT NAMED 'Poulty038'

(50) Latin Name: *Rosa hybrida*
Varietal Denomination: Poulty038

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 54 days.

(21) Appl. No.: 18/831,806

(22) Filed: Sep. 15, 2025

(65) Prior Publication Data

US 2026/0083034 P1 Mar. 19, 2026

(30) Foreign Application Priority Data

Sep. 19, 2024 (QZ) ..... PBR 20242193

(51) Int. Cl.
*A01H 5/00* (2018.01)
*A01H 5/02* (2018.01)
*A01H 6/74* (2018.01)

(52) U.S. Cl.
USPC ..... Plt./122
CPC ..... *A01H 6/749* (2018.05); *A01H 5/02* (2013.01)

(58) Field of Classification Search
USPC ..... Plt./101, 116, 122
See application file for complete search history.

(56) References Cited

U.S. PATENT DOCUMENTS

PP31,548 P2 * 3/2020 Olesen ..... A01H 6/749 Plt./359

* cited by examiner

*Primary Examiner* — Karen M Redden

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulty038'.

This application claims priority to Plant Breeder's Rights Application Number 2024/2193, which was filed at the Community Plant Variety Rights Office in the European Union on Sep. 19, 2024, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2017 and the resulting seeds were planted in a controlled environment in Odense, Denmark. The new variety, named 'Poulty038', originated as a single seedling from the stated cross.

The new variety may be distinguished from its male pollen parent and female seed parent primarily by the following characteristics. Flowers of the male pollen parent plant are Red Group 53B in colour. The new variety has a general flower colour of Red Group 53A. The male pollen parent variety grows to 30 cm in height, while the new variety grows to 23 cm in height. The female seed parent plant has a flower colour of Red Group 45D while 'Poulty038' has a flower colour of Red Group 53B.

The objective of the hybridization of this rose variety was to create a new and distinct variety with unique qualities, such as:

1. Uniform and abundant red flowers;
2. Vigorous, but compact growth when propagated on its own roots;
3. Suitability for commercial production in small containers; and
4. Exceptional disease resistance.

This combination of qualities is not present in previously available commercial cultivars of this type, known to the inventor, and distinguish 'Poulty038' from all other varieties of which we are aware.

As part of the rose development program, Mogens N. Olesen germinated the seeds from the aforementioned hybridization during winter of 2017 and conducted evaluations on the resulting seedlings in a controlled environment in Odense, Denmark. 'Poulty038' was selected in the spring of 2018 by the inventor as a single plant from the progeny of the aforementioned hybridization.

Asexual reproduction of 'Poulty038' by rooted cuttings was first done by Mogens N. Olesen in the nursery in Odense, Denmark in July, 2018. This initial and other subsequent asexual propagations conducted in controlled environments have demonstrated that the characteristics of 'Poulty038' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty038'.

Specifically illustrated in FIG. 1 of the drawings are open flowers viewed from the side and above, flower petals and sepals detached from the receptacle, revealing reproductive flower parts.

Figure 1:
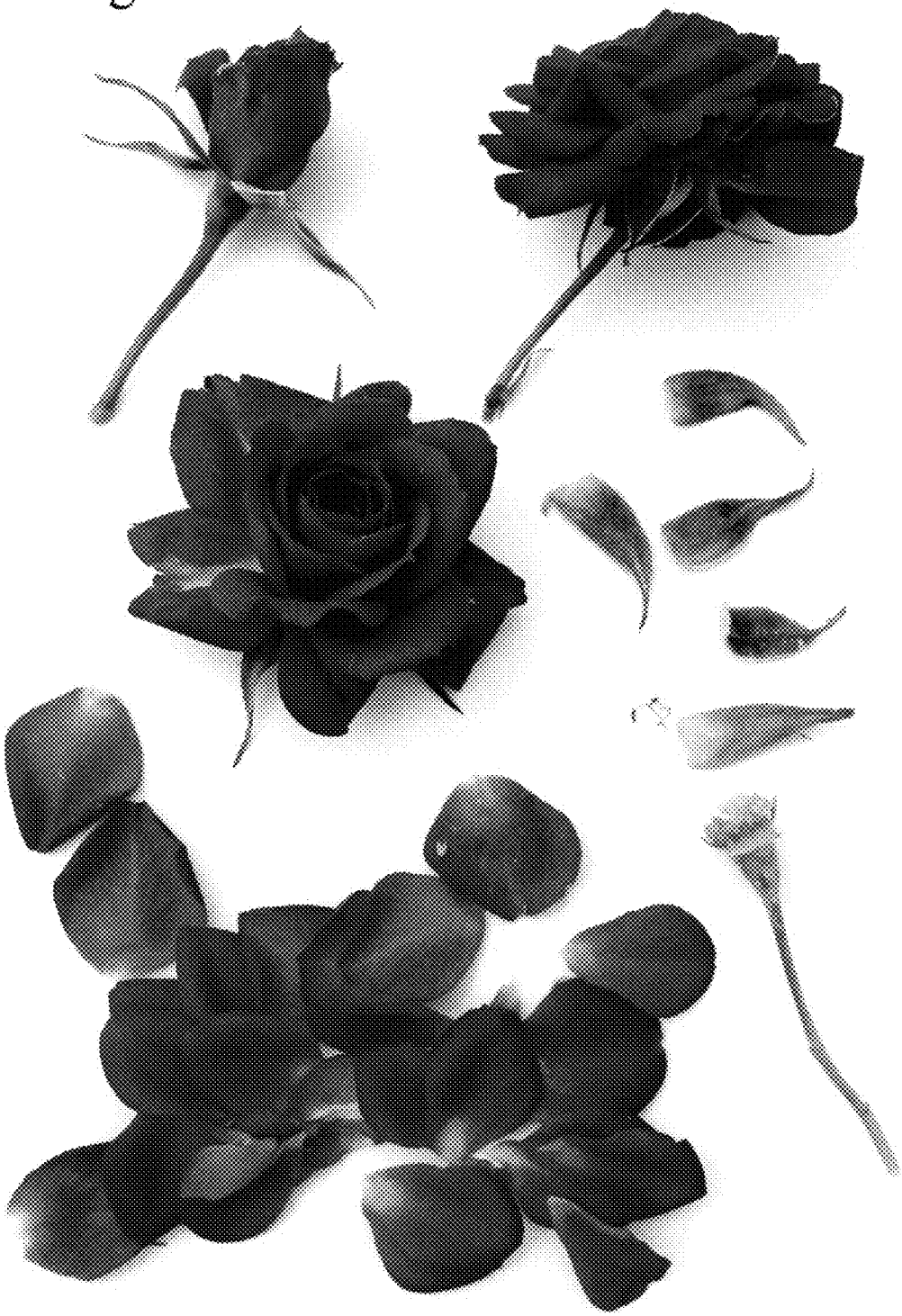
Figure 2:
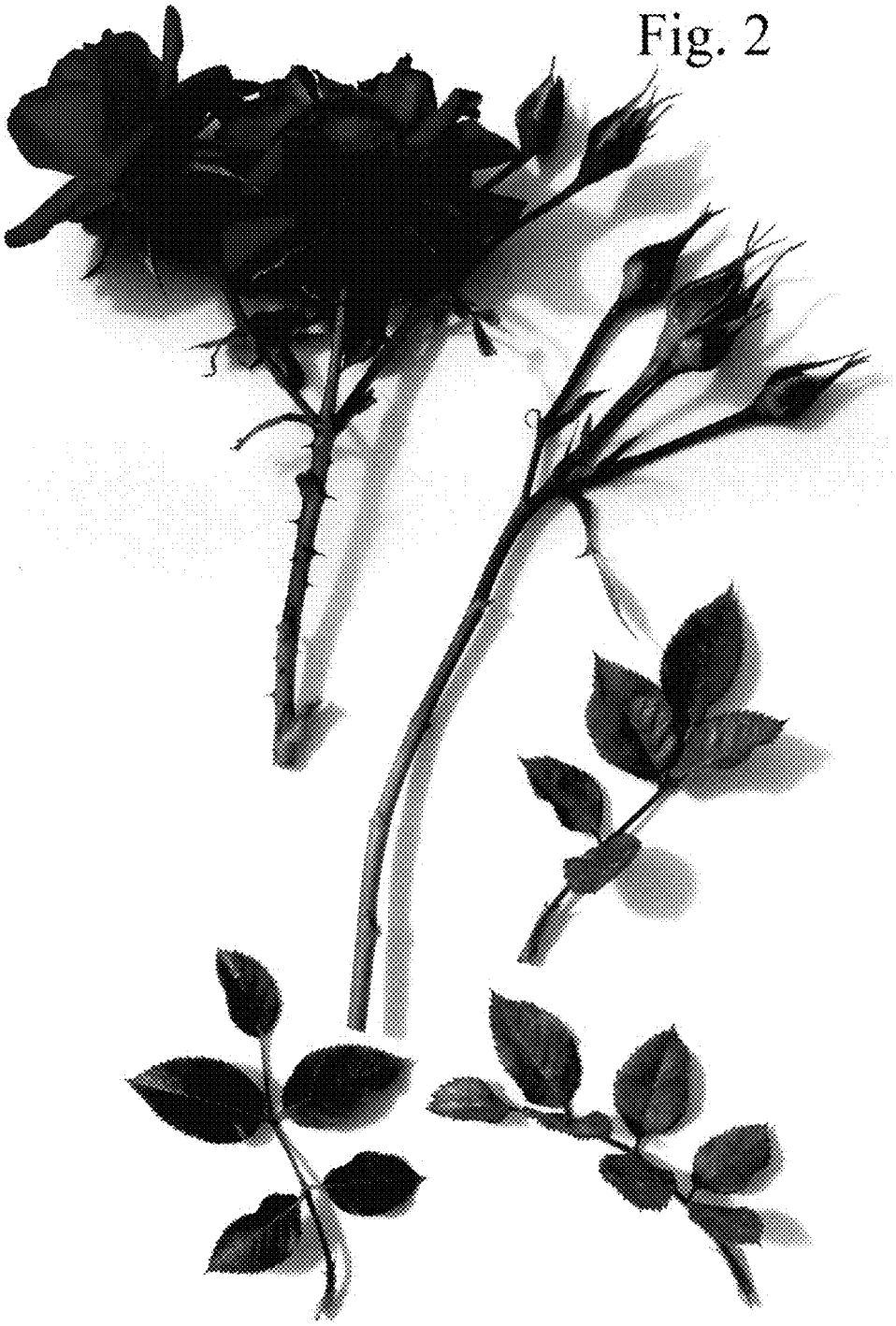

Specifically illustrated in FIG. 2 of the drawings is a cluster of open flowers on the branch, a cluster of flower buds on a branch, juvenile and mature leaves. Plants shown are 12 months of age.

DETAILED DESCRIPTION OF THE VARIETY

The following is a description of 'Poulty038', as observed in its growth in an outdoor nursery in Half Moon Bay, California. Observed plants are 12 months of age, and were grown on their own roots in 24 cm pots. Color references are made using The Royal Horticultural Society (London, England) Colour Chart, 2001, except where common terms of color are used.

For a comparison, several physical characteristics of the rose variety 'Poulpal072', U.S. Plant Pat. No. 31,548 are compared to the claimed plant. The new variety and comparison variety have essentially the same general tonality of flower. 'Poulty038' has 30 flower petals, 'Poulpal072' has 40 flower petals. The claimed plant has a flower diameter of 55 mm while 'Poulpal072' has a flower diameter of 100 mm. 'Poulty038' grows to a mature height of about 21 cm, while 'Poulpal072' grows to a mature height of about 40 cm.

Flower and Flower Bud

Blooming habit: Continuous.

Flower bud:

- *Size*.—Upon opening, 25 to 30 mm in length from base of receptacle to end of bud. Bud diameter is 10 to 13 mm.
- *Bud form*.—Ovoid.
- *Bud color*.—As sepals divide petals are Red-Purple Group N57B and Red-Purple Group 59D.
- *Sepal inner surface*.—Color: Yellow-Green Group 146D with intonations of Greyed-Orange Group 166A. Surface: Lightly pubescent.
- *Sepal outer surface*.—Color: Yellow-Green Group 144A with intonations of Greyed-Orange Group 166B. Texture: Smooth.
- *Sepal shape*.—Apex: Cirrhose. Base: Flat at union with receptacle.
- *Sepal margin*.—Margins have very light foliaceous appendages on three of the five sepals.
- *Sepal size*.—About 29 mm long, 10 mm wide.
- *Receptacle*.—Texture: Smooth. Size: 8 mm in height, 9 mm wide. Color: Yellow-Green Group 144A with intonations of Greyed-Red Group 181A. Shape: Campanulate.
- *Pedicel.—Surface: Smooth. Length:* 31 mm. Diameter: 2 mm on average. Color: Yellow-Green Group 144A with intonations of Greyed-Purple Group 183B. Strength: Strong.
- *Peduncle*.—Length: 2 to 4 cm. Diameter: About 3 mm. Color: Yellow-Green Group 145A with intonations of Greyed-Purple Group 183B. Texture: Smooth.

Flower bud development: Flower buds are borne in clusters of 3 to 5 flower buds per stem.

Flower bloom:

- *Fragrance*.—Moderate honey like perfume.
- *Duration*.—The blooms have a duration on the plant of approximately 14 days. Petals fall cleanly away from plant after flowers have fully matured.
- *Size*.—Flower diameter is 55 mm when open. Flower depth is 23 mm.
- *Flower shape*.—Initially hybrid tea class flower with a high pointed center tightly closed. After flowers mature they become rosette shaped.
- *Shape of flower, side view*.—The upper portion is convex. The lower portion is concave.

Petalage: Under normal conditions, flowers have about 30 petals.

General tonality of flower: Open flowers are Red Group 53A.

Petal color:

- *Upon opening, outer petals*.—Upper surface: Red Group 53A with streaks of White Group 155A. Lower surface: Red-Purple Group 60B, towards middle zone Red-Purple Group 62D.
- *Upon opening, inner petals*.—Upper surface: Red Group 53A. Lower surface: Red-Purple Group 60B, towards middle zone Red-Purple Group 62D.
- *Basal petal spots, upon opening*.—Upper surface: Yellow Group 1C. Lower surface: Yellow Group 1C.
- *After opening, outer petals*.—Upper surface: Red-Purple Group 61B. Petal spot Green-White Group 157A. Lower surface: Red-Purple Group 61B with streaks of Red Group 56C. At basal zone White Group 155A.
- *After opening, inner petals*.—Upper surface: Red-Purple Group 61B. Petal spot Green-White Group 157A. Lower surface: Red-Purple Group 61B with streaks of Red Group 56C. At basal zone White Group 155A.
- *Basal petal spots, after opening*.—Upper surface: White Group 155A. Lower surface: White Group 155A.

Petals:

- *Petal reflex*.—Partially reflexed.
- *Margin*.—Entire and uniform. Moderate undulations.
- *Shape*.—Broad and elliptic. Apex shape: Rounded. Base shape: Acute.
- *Size*.—30 mm (l)×26 mm (w).
- *Texture*.—Smooth.
- *Thickness*.—Average.

Petaloids:

- *Size*.—9 mm (l) by 4 mm (w).
- *Quantity*.—About 5.
- *Shape*.—Elliptical with an acute base and rounded apices.
- *Color*.—The upper surface is Red Group 53A. The lower surface is Red-Purple Group 60B.

Reproductive flower parts:

- *Pollen*.—None observed.
- *Anthers*.—Size: 2 mm in length. Color: Greyed-Orange Group 163B. Quantity: 40 on average.
- *Filaments*.—Color: Yellow Group with intonations of Greyed-Purple Group 58C. Length: 4 mm.
- *Pistils*.—Length: 11 mm. Quantity: 25 on average.
- *Stigmas*.—Color: Green-White Group 157.
- *Styles*.—Color: Green-White Group 157.

*Location of stigmas*.—Superior in location relative to the length of the filaments and the height of the anthers.

*Hips*.—None Observed.

Plant

Plant growth: Upright, and well branched, bushy. Plants are 21 cm in height, and 31 cm wide.

Stems:

*Color of juvenile growth*.—Yellow-Green Group 144B.

*Color of mature growth*.—Yellow-Green Group 144A.

*Length*.—Canes are about 11 cm from the base of the plant to the flowering portion.

*Diameter*.—About 3 mm.

*Internodes*.—On mature canes about 25 mm between nodes.

*Surface texture*.—Young wood: Smooth. Older wood: Rough with many small prickles.

Long prickles:

*Incidence*.—15 prickles per 10 cm of stem.

*Size*.—Average length of prickles on mature stems is 5 mm.

*Shape*.—Upper portion is linear. Lower portion is concave.

*Color*.—Juvenile prickles: Greyed-Purple Group 183C. Mature prickles: Greyed-Purple Group 183C.

Plant foliage:

*Compound leaf*.—81 mm (l)×56 (w).

*Quantity*.—About 3 to 4 leaves per 10 cm of stem on average.

*Leaf bearing angle to the stem*.—45 degrees.

*Color of juvenile foliage*.—Upper side: Yellow-Green Group 144A with Greyed-Purple Group 183B at margins. Lower side: Yellow-Green Group 144B with shades of Greyed-Purple Group 183B.

*Color of mature foliage*.—Upper side: Yellow-Green Group 147A. Lower side: Yellow-Green Group 146B.

Plant leaves and leaflets:

*Stipules*.—Size: 10 mm long, 2 mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 1.5 mm. Upper surface color: Yellow-Green Group 144A with intonations of Greyed-Red Group 180A. Lower surface color: Yellow-Green Group 144A.

*Rachis*.—Length: About 22 mm. Upper surface color: Yellow-Green Group 144A with intonations of Greyed-Red Group 180A. Lower surface color: Yellow-Green Group 144A.

*Leaflet*.—Quantity: Normally 5 leaflets. Margins: Serrated. Size: Terminal leaflets are about 26 mm long,× 16 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty038' substantially as described and illustrated herein.

* * * * *